United States Patent
Sanzari

(10) Patent No.: US 7,049,596 B2
(45) Date of Patent: May 23, 2006

(54) METHOD AND APPARATUS FOR DISTINGUISHING MATERIALS

(75) Inventor: Martin A. Sanzari, Elmwood Park, NJ (US)

(73) Assignee: Innoventive Technologies, Inc., Wayne, NJ (US)

( * ) Notice: Subject to any disclaimer, the term of this patent is extended or adjusted under 35 U.S.C. 154(b) by 258 days.

(21) Appl. No.: 10/613,658

(22) Filed: Jul. 2, 2003

(65) Prior Publication Data

US 2005/0001166 A1    Jan. 6, 2005

(51) Int. Cl.
G01M 21/35    (2006.01)

(52) U.S. Cl. .............. 250/339.11; 250/339.1; 250/341.8

(58) Field of Classification Search .......... 250/339.11, 250/338.1, 339.12, 339.14, 340, 341.1, 341.8, 250/342, 343; 378/83, 88
See application file for complete search history.

(56) References Cited

U.S. PATENT DOCUMENTS

| | | | | |
|---|---|---|---|---|
| 3,980,568 | A * | 9/1976 | Pitchford et al. | 378/46 |
| 4,197,457 | A * | 4/1980 | Cheo | 250/338.1 |
| 4,359,638 | A * | 11/1982 | Allport | 378/88 |
| 4,808,824 | A * | 2/1989 | Sinnar | 250/339.11 |
| 4,945,250 | A | 7/1990 | Fantone et al. | |
| 5,106,387 | A | 4/1992 | Cothren, Jr. et al. | |
| 5,406,082 | A * | 4/1995 | Pearson et al. | 250/339.11 |
| 6,040,198 | A * | 3/2000 | Komiya et al. | 438/16 |
| 6,052,056 | A * | 4/2000 | Burns et al. | 340/583 |
| 6,239,436 | B1 * | 5/2001 | Parker et al. | 250/341.8 |
| 6,504,900 | B1 * | 1/2003 | Kondo et al. | 378/70 |
| 2002/0001364 | A1* | 1/2002 | Opsal et al. | 378/88 |
| 2002/0093651 | A1* | 7/2002 | Roe | 356/301 |
| 2002/0169379 | A1 | 11/2002 | Bostrom et al. | |
| 2005/0163282 | A1* | 7/2005 | Zerle | 378/88 |
| 2005/0190882 | A1* | 9/2005 | McGuire | 378/88 |

* cited by examiner

FOREIGN PATENT DOCUMENTS

EP    1048265    11/2000

OTHER PUBLICATIONS

C. Scholz et al., "DIe Knochenzemententfemung mit dem Laser (Bone Cement Removal with the Laser)", Biomed. Technik 36:5 (1991), 120-128.

*Primary Examiner*—David Porta
*Assistant Examiner*—Faye Polyzos
(74) *Attorney, Agent, or Firm*—Drinker Biddle & Reath LLP

(57) ABSTRACT

An apparatus and method for optically detecting whether a substance is present at an inspection site on a base material based on light reflected from the inspection site. A light module generates light of a first wavelength and light of a second wavelength. A first optical transmission medium directs the light of the first wavelength and the light of the second wavelength to the inspection site. A photodetector receives light reflected from the inspection site and generates a reflection signal corresponding to the reflected light. A second optical transmission medium directs the reflected light from the inspection site to the photodetector. A control module has an input for receiving the reflection signal. Responsive to the reflection signal, the control module generates a first inspection site absorption value corresponding to absorption of the light of the first wavelength that was directed at the inspection site and a second inspection site absorption value corresponding to absorption of the light of the second wavelength that was directed at the inspection site. The control module generates an output signal indicating whether the substance is present at the inspection site responsive to the first and second inspection site absorption values.

21 Claims, 7 Drawing Sheets

METHOD AND APPARATUS FOR DISTINGUISHING MATERIALS

FIELD OF THE INVENTION

The present invention is directed to an apparatus and method for detecting the presence of a substance and, in particular, to an optical system for determining whether the substance is present at an inspection site on a base material by analyzing the absorption and reflection of light directed at the inspection site.

BACKGROUND OF THE INVENTION

Laser ablation is a common surgical technique for removing unwanted matter. For example, in heart surgery, laser ablation is used to remove blockages. However, the use of laser ablation is usually limited to applications where the distinction between matter to be retained and matter to be removed is easily discernible so the laser may be precisely directed. Otherwise, misdirected laser energy may remove or damage matter that should be retained.

In orthopedics, when securing a pin to bone, it is desirable to ensure that the pin is actually being cemented to bone and not to other matter. Polymethyl methacrylate (PMMA) is often used as an adhesive for securing metal pins to bone. When securing a pin to bone, it is desirable to ensure that any remaining PMMA from a previously-installed pin is removed and that the pin is being secured to bone and not to soft tissue, dead bone, or to infected or otherwise unhealthy bone. All unwanted matter must be removed while minimizing the removal of healthy bone.

When a pin that was previously cemented into bone using PMMA is later removed, some PMMA is left behind in the cavity from which the pin was removed. A surgeon may use an arthroscope to look down into the cavity as a visual guide for the surgeon's attempts to remove the PMMA from the surface of the bone. However, looking through an arthroscope, it is difficult to distinguish between PMMA and bone because they are similar in color and because the arthroscope has limited resolution. In some orthopedic procedures, the old PMMA is liquefied to remove the previously-cemented pin and the liquefied PMMA is absorbed into the bone, making the distinction between bone and PMMA more difficult to see.

The difficulty in distinguishing between matter to be removed and matter to be retained makes use of laser ablation or other methods of removal (e.g., scalpel, ultrasound) problematic for orthopedics. Misdirected laser energy, for example, can penetrate bone and remove or damage bone at locations where healthy bone is desired.

Fourier transform infrared (FTIR) spectroscopy techniques may be used to identify materials by measuring their absorption spectra. This technique includes the time consuming steps of taking a biopsy of the sample material, forming a solution of the sample material, and analyzing the solution with a spectrometer. However, the use of FTIR is not practical in a surgical setting where real-time analysis is required because the steps described above are time consuming and must be repeated for each location to be tested. An improved method and apparatus are needed for distinguishing between materials in real time and/or in a harsh surgical environment where contaminants such as bodily fluids are present and visibility may be limited.

SUMMARY OF THE INVENTION

In one aspect, the invention comprises a method for distinguishing between two different materials. Radiation of two different wavelengths is directed at an inspection site where radiation of one of the wavelengths is absorbed by one material more strongly than the other material. The intensity of reflected radiation resulting from the radiation directed at the inspection site is measured. The intensity of the reflected radiation resulting from directed radiation of one of the wavelengths relative to the intensity of the reflected radiation resulting from directed radiation of the other wavelength is used to determine which of the two materials is present at the inspection site.

According to another aspect, the intensity of the reflected radiation resulting from directed radiation of one of the wavelengths is compared to a first absorption reference value to generate a first difference value. The intensity of the reflected radiation resulting from directed radiation of the other wavelength is compared to a second absorption reference value to generate a second difference value. The first and second difference values are compared to determine a comparison value. A comparison value in excess of a preselected number indicates the presence of one of the materials at the inspection site.

According to another aspect, a radiation source is activated to generate radiation of the two different wavelengths. A first band-pass filter that passes radiation of one of the wavelengths is placed between the radiation source and the inspection site. A second band-pass filter that passes radiation of the other wavelength is then placed between the radiation source and the inspection site, in alternating fashion with the first filter.

According to another aspect, the radiation is generated by activating a first coherent radiation source that generates radiation of one of the wavelengths and activating a second coherent radiation source that generates radiation of the other wavelength. The first and second sources may be activated simultaneously, or alternately, or otherwise.

According to another aspect, one of two materials is selectively removed from an inspection site. Radiation of two different wavelengths is directed at an inspection site where radiation of one of the wavelengths is absorbed by one material more strongly than the other material. The intensity of reflected radiation resulting from the radiation directed at the inspection site is measured. The intensity of the reflected radiation resulting from directed radiation of one of the wavelengths relative to the intensity of the reflected radiation resulting from directed radiation of the other wavelength is used to determine which of the two materials is present at the inspection site. One of the materials is selectively removed from the inspection site responsive to the determination.

According to another aspect, an apparatus is provided for distinguishing between two different materials. A radiation module generates radiation of two different wavelengths which is directed to an inspection site. A detector module receives radiation reflected from the inspection site and generates a corresponding reflection signal. A control module receives the reflection signal and determines which of the two materials is present at the inspection site based on the intensity of the reflected radiation resulting from directed radiation of one of the wavelengths relative to the intensity of the reflected radiation resulting from directed radiation of the other wavelength. The control module generates an output signal indicating which of the two materials is present at the inspection site.

According to another aspect, the apparatus includes a first coherent radiation source that generates radiation of one of the wavelengths and a second coherent radiation source that generates radiation of the other wavelength. The control module may alternately or otherwise activate the first and second coherent radiation sources.

According to another aspect, the radiation source includes a quantum cascade laser.

According to another aspect, the radiation source includes a non-coherent radiation source, a first band-pass filter that passes radiation of one of the wavelengths, a second band-pass filter that passes radiation of the other wavelength, and a pulse generator for alternately passing the first and second band-pass filters between the non-coherent radiation source and the inspection site.

Preferably, the two different wavelengths are in the infrared region and, more preferably, are in the mid-infrared region.

BRIEF DESCRIPTION OF THE DRAWINGS

For the purpose of illustrating the invention, there is shown in the drawings a form that is presently preferred; it being understood, however, that this invention is not limited to the precise arrangements and instrumentalities shown.

DETAILED DESCRIPTION OF THE INVENTION

Figure 1:
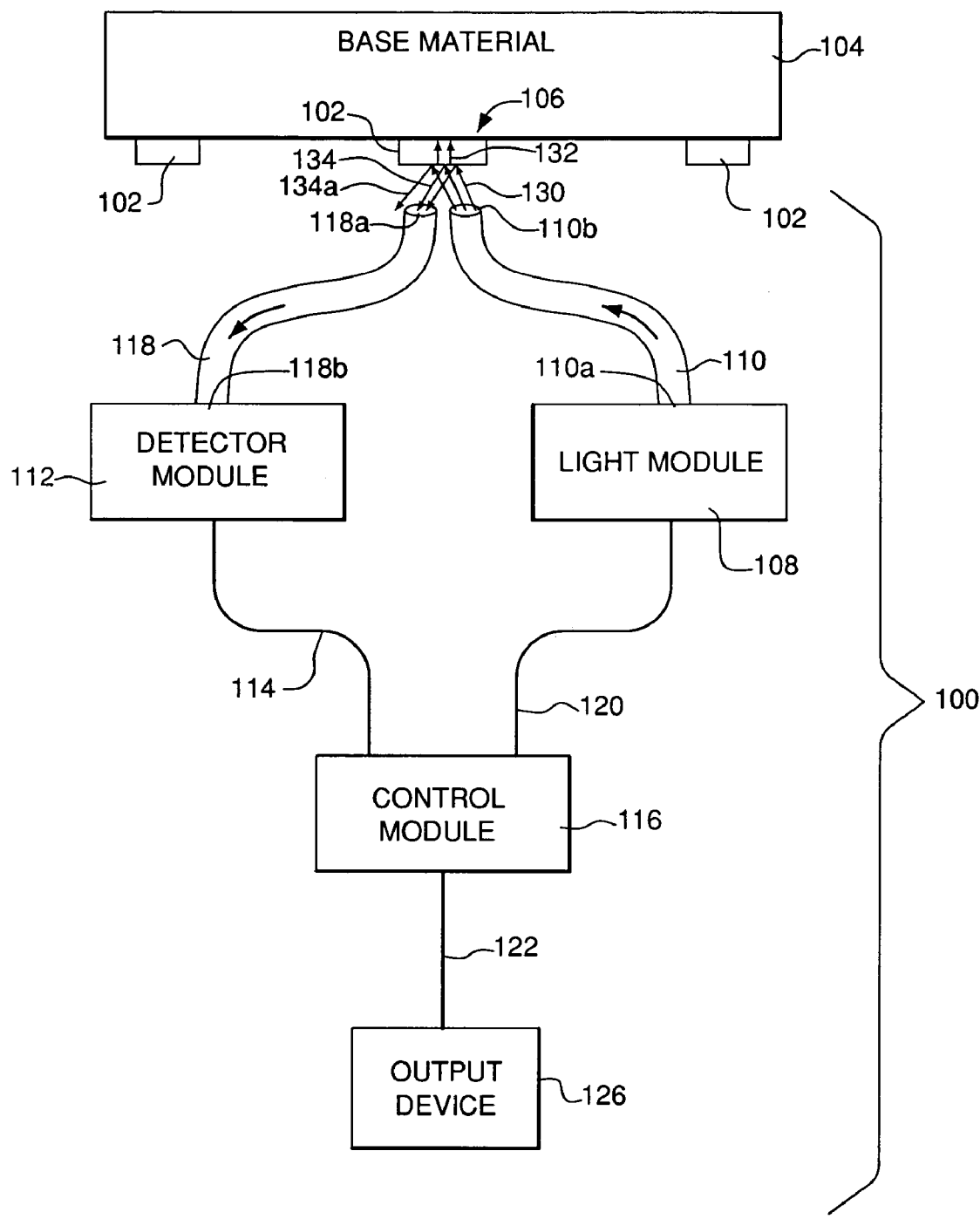
FIG. 1 is a block diagram of an apparatus for determining whether a substance is present on a base material according to an exemplary embodiment of the present invention.

Referring to the drawings, in which like reference numerals illustrate corresponding or similar elements throughout the several views, there is shown in FIG. 1 a block diagram of an apparatus 100 according to an exemplary embodiment of the present invention. The apparatus 100 generates an output signal 122 that indicates whether a substance 102 is present on a base material 104 at an inspection site 106 of the base material 104.

The apparatus 100 includes a light module 108 for generating light of a first wavelength $\lambda_1$ and light of a second wavelength $\lambda_2$. The light of the first and second wavelengths $\lambda_1$, $\lambda_2$ is directed to the inspection site 106 via a first optical transmission medium 110, such as one or more optical fibers. The generated light of the first and second wavelengths $\lambda_1$, $\lambda_2$ enters an input 110a of the first optical transmission medium 110 and exits from its output 110b in a direction toward the inspection site 106.

The light of the first and second wavelengths $\lambda_1$, $\lambda_2$ incident upon the inspection site 106 is either reflected or absorbed by the material (e.g., substance 102 or bone 104) present at the inspection site 106. The incident light is represented in FIG. 1 by arrows 130, the reflected light is represented by arrows 134, and the absorbed light is represented by arrows 132.

The reflected light 134 is received at the input or sensing head 118a of a second optical transmission medium 118, such as one or more optical fibers. The second optical transmission medium 118 conducts the reflected light 134 to its output 118b and, from there, to a detector module 112. The first and second optical transmission mediums 110, 118 may include a crystal at the output 110b and/or the sensing head 118a to concentrate and collect the incident and reflected light. The crystal may be positioned in contact with the inspection site 106 for directing the incident light 130 to and receiving the reflected light 134 from the inspection site 106.

The detector module 112 receives the reflected light 134 from the output 118b of the second optical transmission medium 118 and generates a reflection signal 114 indicating the amount or intensity of reflected light it receives. The control module 116 monitors and/or controls the generation of light by the light module 108 via a light control signal 120 and uses the reflection signal 114 to generate an output signal 122 indicating whether the substance 102 is present on the base material 104 at the inspection site 106.

Different materials have different absorption spectra. One material may absorb more light of a particular wavelength than does a different material. The control module 116 uses this characteristic of materials to determine whether the substance 102 is present at the inspection site 106 and generate the output signal 122.

Figure 2A:
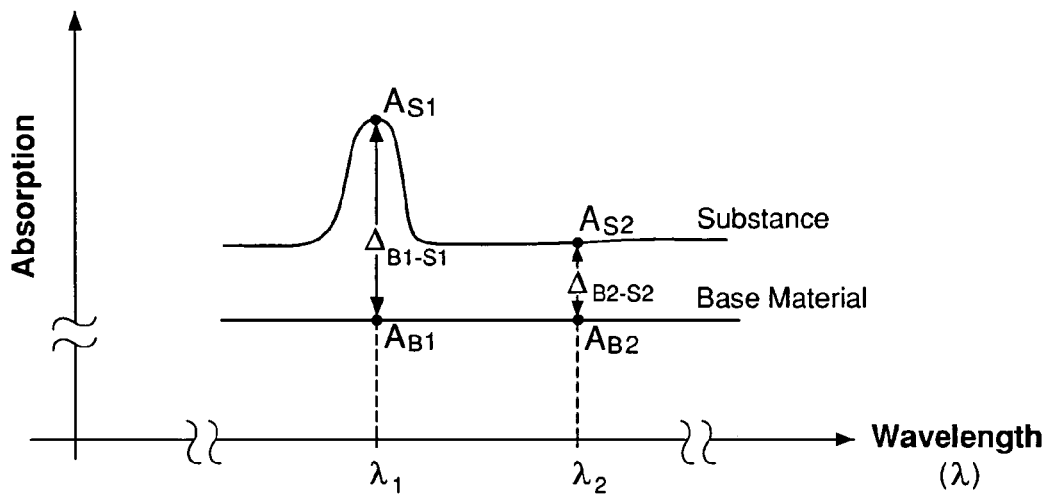
FIG. 2A is a chart showing exemplary absorption spectra for a base material and a substance that may be located upon the base material.

Exemplary absorption spectra of the base material 104 and of the substance 102 are shown in FIG. 2A. The substance 102 has first and second substance absorption values $A_{S1}$, $A_{S2}$ corresponding to the absorption by the substance 102 of light of the first and second wavelengths $\lambda_1$, $\lambda_2$, respectively. The base material 104 has first and second base absorption values $A_{B1}$, $A_{B2}$ corresponding to the absorption by the base material 104 of light of the first and second wavelengths $\lambda_1$, $\lambda_2$, respectively.

The absorption spectrum of the substance 102 has a peak at the first wavelength $\lambda_1$ relative to the absorption spectrum of the base material 104. Neither the substance 102 or the base material 104 have an absorption peak at the second wavelength $\lambda_2$. This results in the difference $\Delta_{B1-S1}=|A_{B1}-A_{S1}|$ in absorption values at the first wavelength $\lambda_1$ being significantly greater than the difference $\Delta_{B2-S2}=|A_{B2}-A_{S2}|$ in absorption values at the second wavelength $\lambda_2$.

The first and second wavelengths $\lambda_1$, $\lambda_2$ are selected, based on the particular absorption spectra of the substance 102 and the base material 104, so the difference between $\Delta_{B1-S1}=|A_{B1}-A_{S1}|$ and $\Delta_{B2-S2}=|A_{B2}-A_{S2}|$ is substantial. In other words, one of the first and second wavelengths $\lambda_1$, $\lambda_2$ is selected so light of that wavelength is strongly absorbed by either the base material 104 or by the substance 102, relative to absorption by the other, so the difference between $\Delta_{B1-S1}=|A_{B1}-A_{S1}|$ and $\Delta_{B2-S2}=|A_{B2}-A_{S2}|$ is substantially large and easy to measure. The first and second wavelengths $\lambda_1$, $\lambda_2$ are preferably selected so the difference between $\Delta_{B1-S1}$ and $\Delta_{B2-S2}$ is greater than the tolerances or error in the techniques used to measure the absorption values. The control module 116 uses the difference between $\Delta_{B1-S1}$ and $\Delta_{B2-S2}$ to determine whether the incident light 130 of the first and second wavelengths $\lambda_1$, $\lambda_2$ is directed at the substance 102 or the base material 104 at the inspection site 106. Operation of control module 116 is explained with reference to FIG. 2B.

Figure 2B:
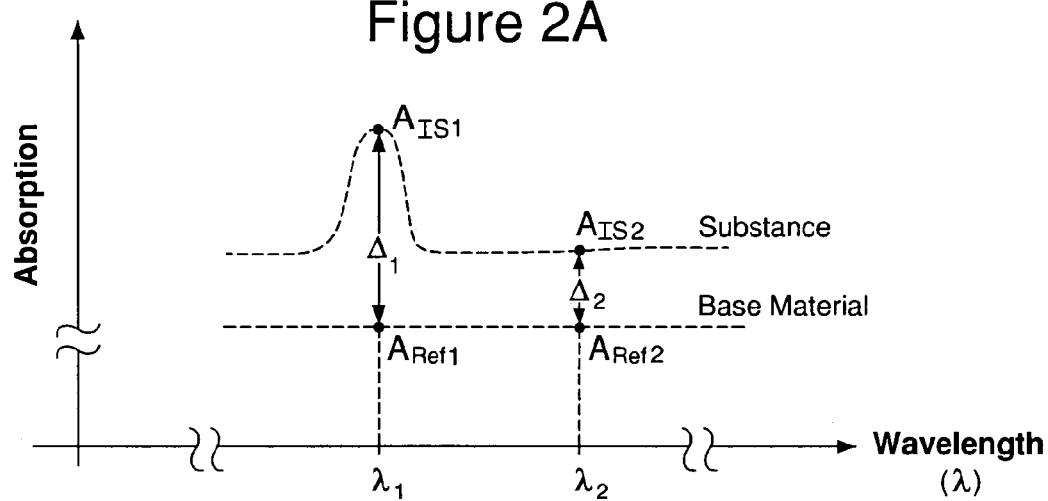
FIGS. 2B–2C are charts showing exemplary absorption spectra and values for an exemplary base material, substance and inspection site.

The absorption spectra of the substance 102 and the base material 104 are shown in phantom in FIG. 2B. The control module 116 uses the reflection signal 114 received from the detection module 112 to calculate absorption values $A_{IS1}$, $A_{IS2}$ for light of each of the first and second wavelengths $\lambda_1$, $\lambda_2$ directed at the inspection site 106, interpreting the absence of reflected light as absorption.

The control module compares the absorption $A_{IS1}$ of light of the first wavelength $\lambda_1$ directed to the inspection site 106 to a first absorption reference value $A_{Ref1}$ and generates a first difference value $\Delta_1 = |A_{IS1} - A_{Ref1}|$. The control module 116 also compares the absorption $A_{IS2}$ of light of the second wavelength $\lambda_2$ directed to the inspection site 106 to a second absorption reference value $A_{Ref2}$ and generates a second difference value $\Delta_2 = |A_{IS2} - A_{Ref2}|$. In this exemplary embodiment, the first and second absorption reference values $A_{Ref1}$, $A_{Ref2}$ are equal to the first and second base absorption values $A_{B1}$, $A_{B2}$.

The control module 116 then compares the first difference value $\Delta_1$ to the second difference value $\Delta_2$. The result of this comparison indicates whether the substance 102 is present at the inspection site 106. In an exemplary embodiment, the control module 116 compares the first and second difference values by generating a comparison value $CV = |\Delta_1 - \Delta_2|$ and comparing the comparison value to one or more threshold or preselected values or numbers. If the comparison value CV exceeds a first threshold value, the control module 116 generates an output signal 122 indicating that the substance 102 is present at the inspection site 106. If the comparison value CV is less than a second threshold value that is less than the first threshold value, the control module 116 generates an output signal 122 indicating that the substance 102 is absent from the inspection site 106.

Alternatively, the first and second absorption reference values $A_{Ref1}$, $A_{Ref2}$ could equal the first and second substance absorption values $A_{S1}$, $A_{S2}$. In such case, if the comparison value CV exceeds a first threshold value, the control module 116 generates an output signal 122 indicating that the substance 102 is absent from the inspection site 106. If the comparison value CV is less than a second threshold value, the control module 116 generates an output signal 122 indicating that the substance 102 is present at the inspection site 106.

In the above example, the first threshold value is greater than the second threshold value. If the comparison value CV falls between the first and second threshold values, the control module 116 generates an output signal 122 indicating that whether the substance 102 is present at the inspection site 106 is indeterminate. In another exemplary embodiment, the first and second threshold values are equal.

In an exemplary embodiment, the first and second wavelengths $\lambda_1$, $\lambda_2$ are selected so the absorption values of the substance $A_{S1}$, $A_{S2}$ are approximately equal and the first and second absorption values of the base material $A_{B1}$, $A_{B2}$ are significantly different. The difference between $\Delta_{B1-S1} = |A_{B1} - A_{S1}|$ and $\Delta_{B2-S2} = |A_{B2} - A_{S2}|$ then simplifies to approximately $|A_{B1} - A_{B2}|$. The control module 116 may then determine whether the substance 102 is present at the inspection site 106 by comparing the first inspection site absorption value $A_{IS1}$ to the second inspection site absorption value $A_{IS2}$. If these values are approximately equal, the control signal 122 indicates that the substance 102 is present and if they are significantly different (e.g., difference exceeds a threshold), the control signal 122 indicates that substance 102 is absent from the inspection site 106.

The first and second wavelengths $\lambda_1$, $\lambda_2$ may similarly be selected so the absorption values of the base material $A_{B1}$, $A_{B2}$ are approximately equal and the first and second absorption values of the substance $A_{S1}$, $A_{S2}$ are significantly different. In such case, if the first inspection site absorption value $A_{IS1}$, and the second inspection site absorption value $A_{IS2}$ are approximately equal, the control signal 122 indicates that the substance 102 is absent from the inspection site 106 and if they are significantly different (e.g., difference exceeds a threshold), the control signal 122 indicates that substance 102 is present at the inspection site 106.

The output signal 122 is generated, as described above, by comparing an absorption value calculated for light of one wavelength to another absorption value calculated for light of another wavelength. The relative determination improves reliability of the output signal 122 because it reduces possible errors that may result from tolerances in the techniques used to measure the absorption of light. For example, a calculated absorption value may be inaccurate if the light of the first and second wavelengths $\lambda_1$, $\lambda_2$ is not properly focused on the inspection site or due to differences in the position or angle of the incident light and/or the sensing head 118a during measurement. The presence of the substance 102 is accurately determined despite potentially inaccurate measurement because the errors are cancelled out or reduced by the method of relative determination as illustrated by the following non-limiting example.

If the incident light 130 is directed to the inspection site 106 at an angle such that some of the reflected light 134a is not received by the sensing head 118a of the second optical transmission medium 118, this reflected light 134a will not be detected by the detector module 112. The control module 116 may misinterpret the absence of this reflected light 134a as absorption and calculate a corresponding absorption value that is higher than the actual absorption by material present at the inspection site 106. This can be understood with reference to FIG. 2C for an example where only the base material 104 (and not the substance 102) is present at the inspection site 106. The first and second inspection site absorption values $A_{IS1}$, $A_{IS2}$ calculated by the control module 116 would be greater than the true absorption values $A_{B1}$, $A_{B2}$ for the base material (shown in phantom) because undetected reflected light 134a is, in this example, not received by the detector module 112. This results in both the first and second difference values $\lambda_2$, $\lambda_2$ appearing greater in value than they would be if the true first and second inspection site absorption values $A_{IS1}$, $A_{IS2}$ were generated.

However, this does not affect the accurate determination of whether the substance 102 is present at the inspection site 106 because that determination is based on the difference between the first difference value $\Delta_1 = |A_{IS1} - A_{Ref1}|$ and the second difference value $\Delta_2 = A_{IS2} - A_{Ref2}$, and the effect of the undetected reflected light 134a in these values cancels.

Figure 2C:
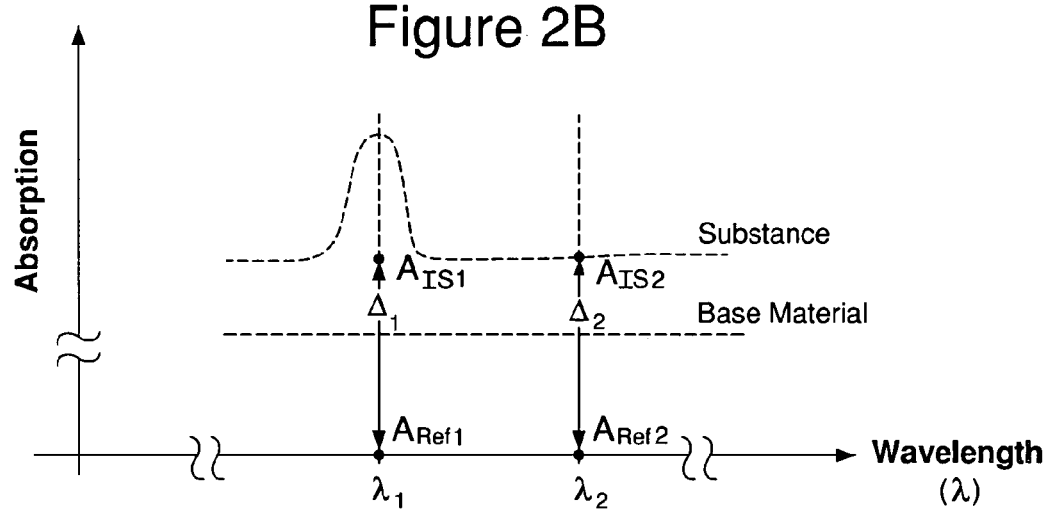

As illustrated graphically in FIG. 2C, the difference between $\Delta_1$ and $\Delta_2$ is insignificant (e.g., less than a threshold value), thereby correctly indicating that the base material 104 (and not the substance 102) is present at the inspection site 106. Thus, the present invention accurately determined whether the substance 102 was present at the inspection site 106 despite not detecting reflected light 134a. False positives are thereby avoided.

The example described above with regard to FIG. 2C illustrates how the direction of the incident light 130 relative to the surface of the inspection site 106 may affect the measured inspection site absorption values $A_{IS1}$, $A_{IS2}$. In an extreme, the measured inspection site absorption value $A_{IS1}$, $A_{IS2}$ will have a maximum when the incident light 130 is directed away from the inspection site. Other operating conditions may affect measured absorption such as contaminants or other materials present at the inspection site 106. The threshold values may be adjusted higher or lower based on measured absorption values to account for variations in operating conditions.

The absorption spectra shown in FIGS. 2A–2C are illustrated by plots that are not to scale and are exaggerated to illustrate the teachings of the present invention. The peak in the absorption of the substance 102 at the first wavelength $\lambda_1$ is used for illustration purposes only. It is not necessary that the substance 102 have a peak in its absorption spectrum at the first or second wavelengths $\lambda_1$, $\lambda_2$ provided that there is a significant difference between $\Delta_{B1-S1}=|A_{B1}-A_{S1}|$ and $\Delta_{B2-S2}=|A_{B2-AS2}|$.

In the exemplary embodiment shown in FIGS. 2A–C, neither the base material 104 nor the substance 102 has a peak absorption of light at the second wavelength 2. This characteristic may be used to identify an inaccurate calculated absorption value $A_{IS2}$ for light of the second wavelength if such calculated value corresponds to a peak absorption value. For example, if the control module 116 calculates a second inspection site absorption value $A_{IS2}$ having a value significantly greater than a generated first inspection site absorption value $A_{IS1}$, the control module may generate an output signal 122 indicating an error rather than whether the substance 102 is present at the inspection site 106. Alternatively, the control module may discard the value and generate the output signal 122 based on another calculated second inspection site absorption value $A_{IS2}$, based on an average of measured inspection site absorption values, or based on another statistical representation of the inspection site absorption values.

Figure 3:
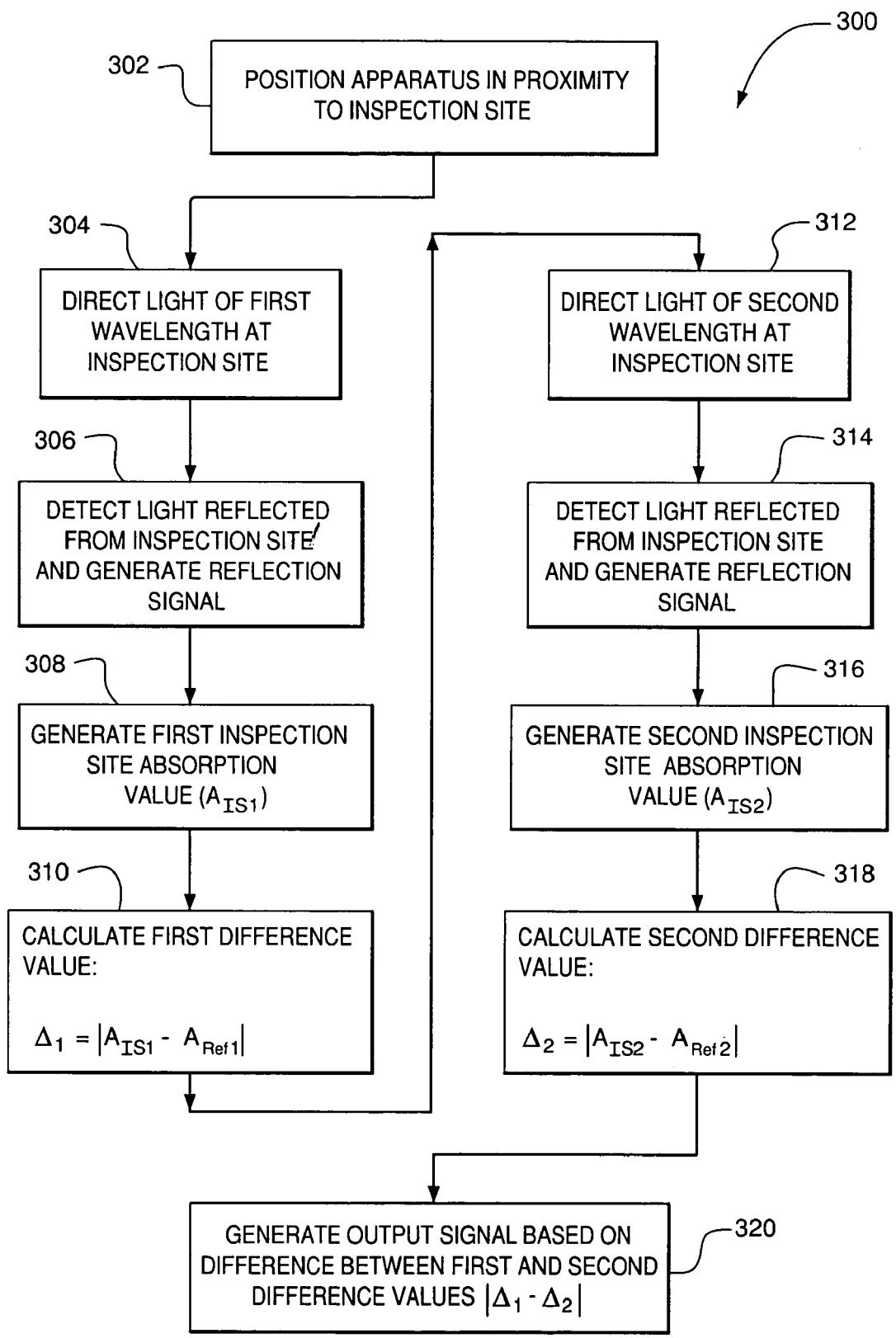
FIG. 3 is a flow chart of a method for determining whether a substance is present on a base material according to an exemplary embodiment of the present invention.

Operation of the apparatus 100 is described with reference to the flow chart 300 of FIG. 3 for a base material 104 having a first base absorption value ($A_{B1}$) and a second base absorption value ($A_{B2}$) corresponding to the base's absorption of light of the first and second wavelengths $\lambda_1$, $\lambda_2$, respectively. The apparatus 100 is first positioned (step 302) in proximity to an inspection site 106. The light module 108 then directs light (step 304) of a first wavelength $\lambda_1$ to the inspection site 106 via the first optical transmission medium 110. The detector module 112 receives the resulting reflected light via the second optical transmission medium 118 and generates a corresponding reflection signal 114 (step 306).

The control module 116 receives the reflection signal 114 and generates a first inspection site absorption value ($A_{IS1}$) corresponding to the absorption of the light of the first wavelength $\lambda_1$ that was directed to the inspection site 106 (step 308). The control module 116 then calculates (step 310) the difference between the first inspection site absorption value ($A_{IS1}$) and the first base absorption value ($A_{B1}$) to generate a first difference value ($\Delta_1$).

The light module 108 then directs light (step 312) of a second wavelength $\lambda_2$ to the inspection site 106 via the first optical transmission medium 110. The detector module 112 receives the resulting reflected light via the second optical transmission medium 118 and generates a corresponding reflection signal 114 (step 314).

The control module 116 receives the reflection signal 114 and generates a second inspection site absorption value $A_{IS2}$ corresponding to the absorption of the light of the second wavelength $\lambda_2$ that was directed to the inspection site 106 (step 316). The control module 116 calculates (step 318) the difference between the second inspection site absorption value $A_{IS2}$ and the second base absorption value $A_{B2}$ to generate a second difference value $A_2$. The control module 116 then calculates a comparison value CV and generates the output signal 122 (step 320) indicating whether the substance 102 is present at the inspection site 106 as described above with reference to FIGS. 2B–2C.

The performance of the apparatus 100 may vary as components of the apparatus 100 degrade over time and use. For example, the intensity of light generated by the light module 108 may decrease over time or the attenuation of the light transmission mediums 110, 118 may increase over time. The apparatus 100 may be calibrated to avoid errors resulting from apparatus 100 variations. Such calibration may improve the accuracy of the apparatus over time and use as performance of the apparatus 100 varies. The apparatus 100 may be calibrated by directing light of the first and second wavelengths $\lambda_1$, $\lambda_2$ at an inspection site 106 known to comprise only the base material in order to determine the base absorption values $A_{B1}$, $A_{B2}$, that are used to determine whether the substance is present at the inspection site 106.

In order to generate the first or second inspection site absorption values $A_{IS1}$, $A_{IS2}$, the control module 116 must correlate the reflection signal 114 to the particular wavelength of light (e.g., $\lambda_1$ or $\lambda_2$) reflected by the inspection site 106 to generate such reflection signal 114. The control module 116 may use the light control signal 120 to control the light module 108 to generate light of the first and second wavelengths $\lambda_1$, $\lambda_2$. The reflection signal 114 may then be correlated to one of the first or second wavelengths $\lambda_1$, $\lambda_2$ of light, depending upon which wavelength the control module 116 instructed the light module 108 to generate at the approximate time that the reflection signal 114 was received. Alternatively, the light module 108 may independently and alternately generate light of the first and second wavelengths $\lambda_1$, $\lambda_2$. The light module 108 may indicate to the control module 116 on the light control signal 120 which wavelength of light is being transmitted to enable control module 116 to correlate the reflection signal 114 to one of the first or second wavelengths $\lambda_1$, $\lambda_2$.

Figure 4:
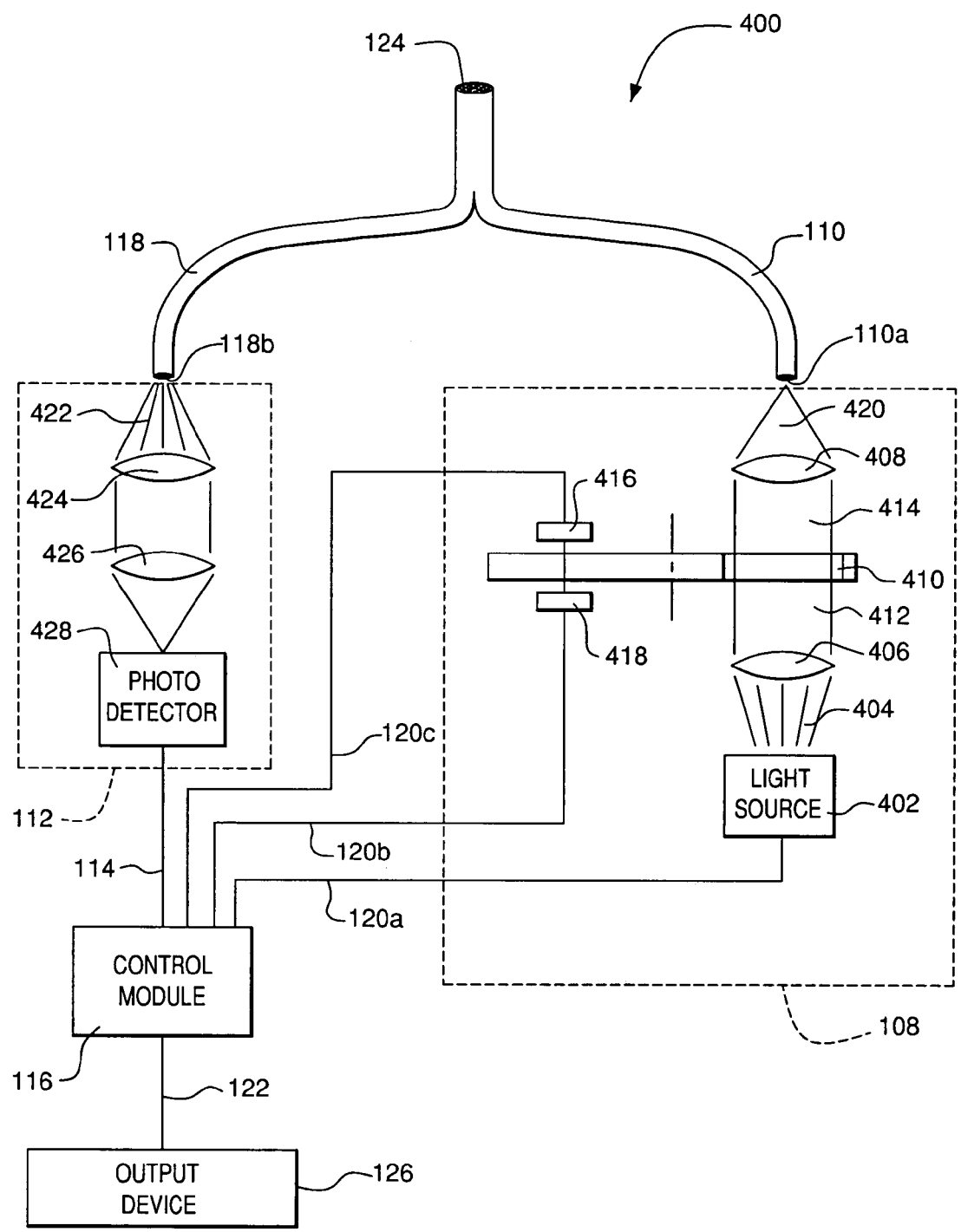
FIG. 4 is a diagram of an apparatus for determining whether a substance is present on a base material according to another exemplary embodiment of the present invention.

An exemplary apparatus 400 according to the present invention is shown in FIG. 4. The light module 108 includes a light source 402 that generates non-coherent light 404. The control module 116 controls operation of the light source 402 via a control signal 120a. The non-coherent light 404 generated by the light source 402 is collimated by a collimating lens 406 into a collimated beam 412.

A band-pass pulse generator 410 converts the collimated non-coherent light beam 412 into alternating beams 414 of collimated light of the first wavelength $\lambda_1$ and of the second wavelength $\lambda_2$. The beams of light 414 are directed to a focusing lens 408 that focuses a beam 420 of light of the first or second wavelengths $\lambda_1$, $\lambda_2$ onto the input 11a of the first optical transmission medium 110. The first optical transmission medium 110 directs the focused light 420 to the inspection site 106.

Figure 5A:
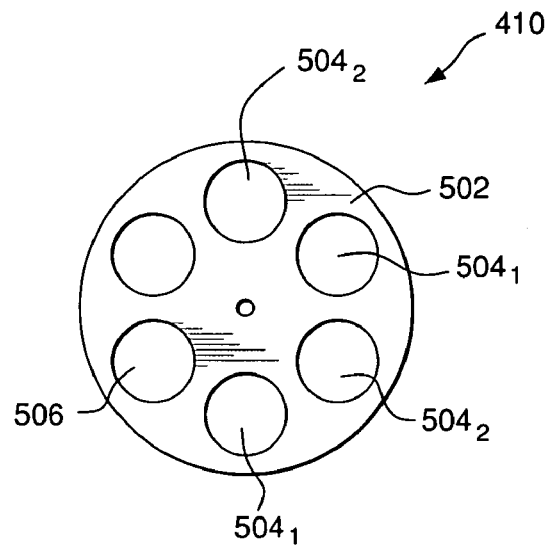
FIGS. 5A–5D are exemplary band-pass pulse generators.

An exemplary band-pass pulse generator 410 is shown in FIG. 5A. The band-pass pulse generator 410 includes a wheel 502 having a plurality of band-pass filters 504. Each band-pass filter 504 allows only light of a narrow band of wavelengths, in this case centered on the first wavelength $\lambda_1$ or the second wavelength $\lambda_2$, to pass through the filter 504. The band-pass filters 504, that pass light of the first wavelength $\lambda_1$ and the band-pass filters $504_2$ that pass light of the second wavelength $\lambda_2$ are alternately arranged around the wheel. Alternating beams of light of the first and second wavelengths $\lambda_1$, $\lambda_2$ pass through the filters as the wheel 502 is rotated by a rotating mechanism (not shown) in the path of the collimated non-coherent beam 412.

Figure 5B:
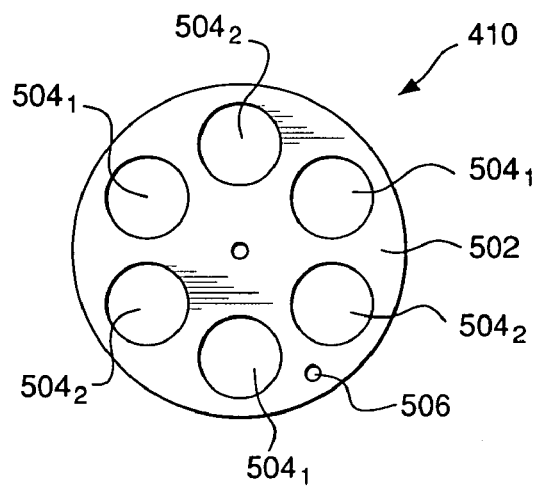
Figure 5C:
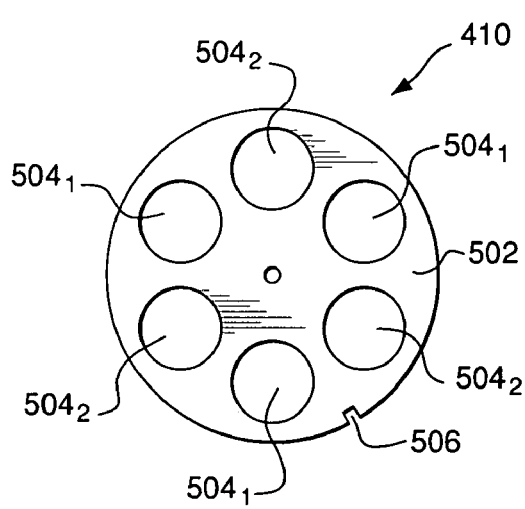

The wheel 502 includes at least one aperture 506 which is used to identify the position of the wheel 502. As the wheel 502 rotates, a photodetector 418 (see FIG. 4) detects light from a light source such as a light emitting diode (LED) 416 as the aperture 506 passes between the photodetector 418 and LED 416. The control module 116 controls operation of the light source 416 via a control signal 120c. The photodetector 418 transmits a signal 120b to the control module 116 indicating when light is detected. The control module 116 determines the position of the wheel based on the signal 120b and the speed of rotation of the wheel 502. The control module 116 uses the position of the wheel 502 to determine which filter is located between the collimating lens 406 and focusing lens 408 to determine when each wavelength of light is being generated. As previously described, the control module 116 then correlates the reflection signal 114 to one of the first and second wavelengths of light $\lambda_1$, $\lambda_2$ incident on the inspection site 106. As illustrated in FIGS. 5B and 5C, at least one aperture 506 may be located separate from and may vary in size from the apertures for the band-pass filters. The aperture 506 may also take the form of a notch 506 as shown in FIG. 5C.

Figure 5D:
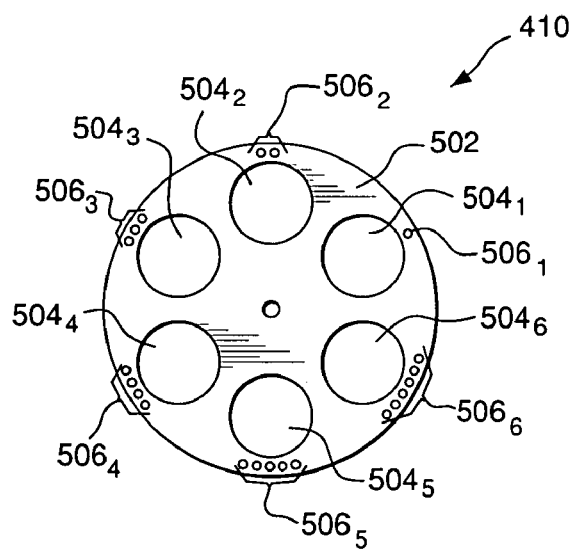

The wheel 502 may include one or more apertures 506 corresponding to each band-pass filter 504 so that a signal is generated by the photodetector 418 corresponding to each separate beam of light directed to the inspection site 106. For example, as shown in FIG. 5D, the wheel 502 includes six different band-pass filters $504_{1-6}$. The wheel 502 includes a pattern of apertures $506_{1-6}$ corresponding to each of the respective band-pass filters $504_{1-6}$. As the wheel rotates, the control module 116 determines the position of the wheel based on the detected pattern or sequence of the signal 120b. For example, if the photodetector 418 and the light source 416 are positioned on a side of the wheel 502 opposite from the collimated beam 412, the control module 116 will correlate a sequence of three pulses on the signal 120b with the collimated beam 412 being directed to the sixth band-pass filter 5046. As illustrated by this example, the present invention can distinguish between more than two materials depending on the wavelengths chosen and the absorption spectra of the different materials.

Figure 6:
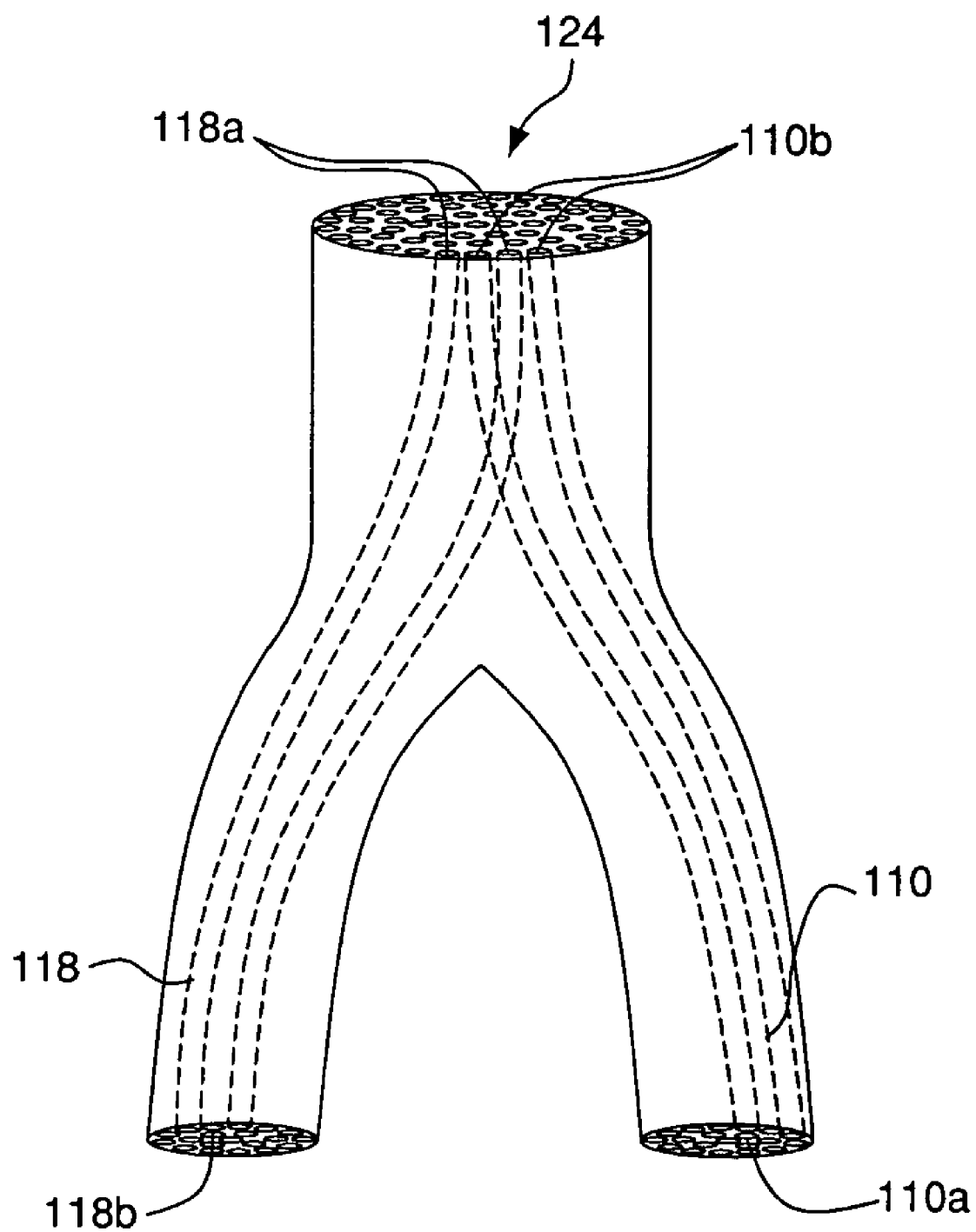
FIG. 6 is a y-type optical fiber bundle used for directing light to an inspection site and for directing light reflected from the inspection site.

In this exemplary embodiment shown in FIG. 4, the first and second optical transmission mediums 110, 118 are implemented by a single Y-type bundle of optical fibers as shown in FIG. 6. Such bundles are known. Selected optical fibers in the bundle function as the first optical transmission medium 110 and transmit light from the light module 108 to the inspection site 106. Other selected optical fibers in the bundle function as the second optical transmission medium 118 and transmit reflected light from the sensing head 124 to the detector module 112. The exemplary detector module 112 shown in FIG. 4 includes a collimating lens 424 for collimating the light 422 exiting received from the output 118b of the second optical transmission medium 118. A focusing lens 426 focuses the collimated light onto a photodetector 428 which generates the reflection signal 114.

In an alternate embodiment, the band-pass pulse generator 410 is incorporated into the detector module 112 instead of in the light module 108. In this configuration, non-coherent light is directed to the inspection site 106 and the reflected light 134 is filtered to separate reflected light 134 resulting from incident light of the first wavelength $\lambda_1$ from reflected light resulting from incident light of the second wavelength $\lambda_2$. The band-pass pulse generator 410 may be configured to alternately position its band-pass filters 504 between the collimating lens 424 and the focusing lens 426 of the detector module 112. The band-pass pulse generator 410 would then convert the collimated non-coherent light beam 412 into alternating beams 414 of collimated light of the first wavelength $\lambda_1$ and of the second wavelength $\lambda_2$.

Figure 7:
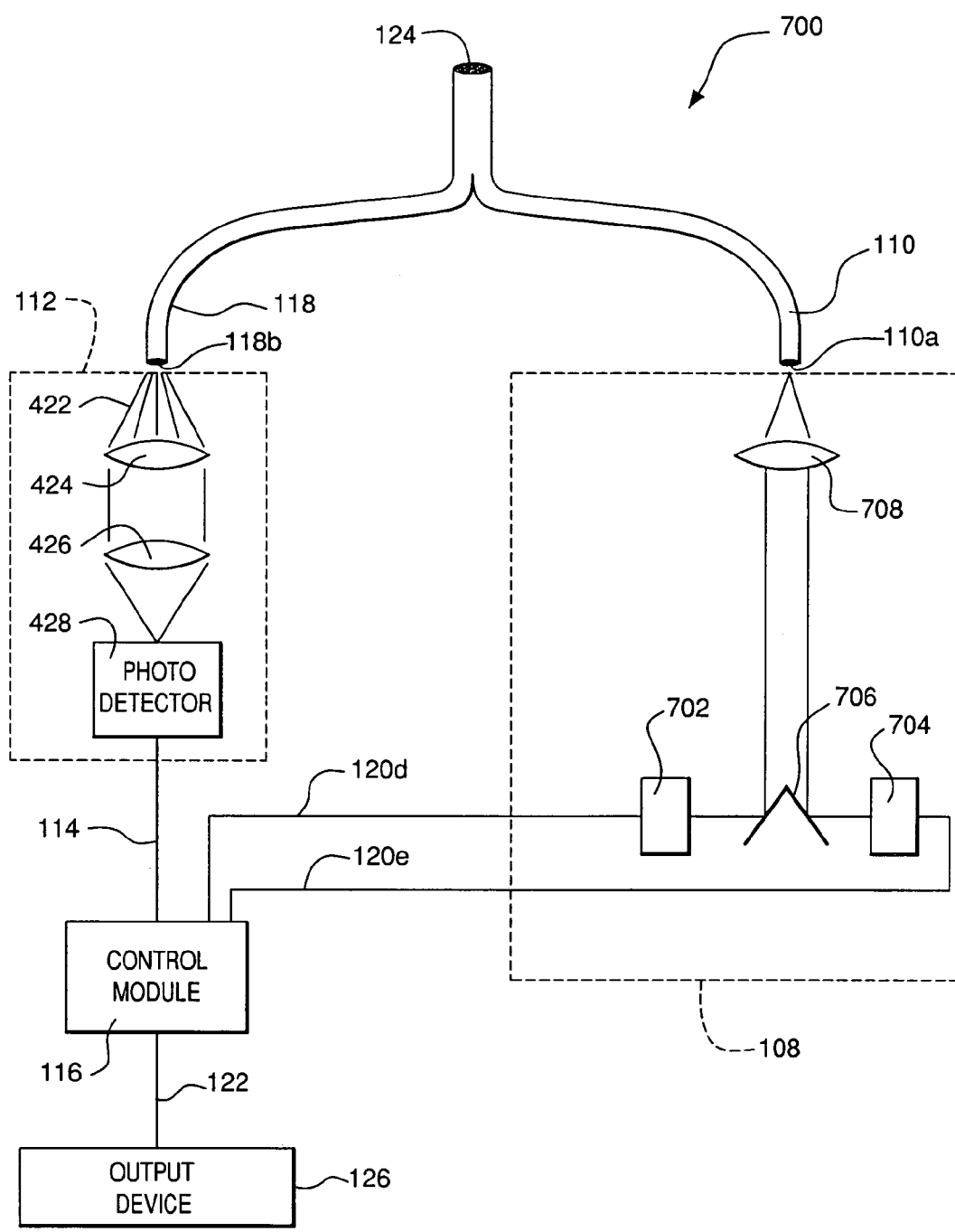
FIG. 7 is a block diagram of an apparatus for determining whether a substance is present on a base material according to another exemplary embodiment of the present invention.

Another exemplary light module 108 is illustrated in the apparatus 700 shown in FIG. 7. The light module 108 includes two coherent light sources 702, 704 such as lasers. One laser 702 generates light of the first wavelength $\lambda_1$ and the other laser 704 generates light of the second wavelength $\lambda_2$.

The light control signal 120 includes a first light control signal 120d for activating the first laser 702 and a second light control signal 120e for activating the second laser 704. The control module 116 controls and alternately pulses the first and second lasers 702, 704. The light from the lasers 702, 704 is directed to a reflector 706 that directs the generated light to a focusing lens 708 for focusing the light on the input 110a of the first optical transmission medium 110. The light module 108 of FIG. 7 may have improved performance and reliability over that of FIG. 7 because it eliminates moving parts (e.g., the rotating wheel 502) that are subject to mechanical failure and eliminates a lens and filter which are a source of signal loss. In an exemplary embodiment, the two coherent light sources 702, 704 are quantum cascade lasers. A quantum cascade laser also provides the advantage of being a low power laser that is bright enough for the purpose of the invention, to distinguish between bone and unwanted matter, while not powerful enough to damage tissue.

In another exemplary embodiment, the light module 108 includes a quantum cascade laser that generates pulses of light of each of the first and second wavelengths $\lambda_1$, $\lambda_2$. The light of the first and second wavelengths $\lambda_1$, $\lambda_2$ generated by the quantum cascade laser may then be filtered by a band-pass pulse generator as describe above. Alternatively, the control module 116 may synchronize its calculation of absorption values $A_{IS1}$, $A_{IS2}$ based on the reflection signal 114 to coincide with the timing of pulses of light of the of the first and second wavelengths $\lambda_1$, $\lambda_2$ generated by the quantum cascade laser.

The output signal 122 (FIGS. 1, 4, 7) is directed to an output device 126. The output device 126 may be a display panel, an audible tone generator, or other indicator for communicating which material is present at the inspection site 106. For example, an audible tone generator may generate an audible tone of one frequency to indicate presence of the substance 102 at the inspection 106 site and generate an audible tone of another frequency (or no tone at all) to indicate absence of the substance at the inspection site 106. The output 110b and sensing head 118b of the apparatus 100 may be scanned across multiple inspection sites while the output device indicates whether a substance is present at each inspection site in real-time.

The output device 126 may be an endoscope or an arthroscope. In an exemplary embodiment, the output device 126 is a removal device used to selectively remove material from the inspection site 106 in response to the output signal 122. The removal device may be configured to remove material from the inspection site 106 while the output signal 122 indicates that the substance 102 is present and not remove material from the inspection site 106 when the output signal 122 indicates that the substance 102 is not present. The removal device may selectively remove material from the inspection site 106 by laser, scalpel, ultrasonic or other techniques for material removal.

In an exemplary embodiment, the light of the first wavelength and the light of the second wavelength are in the infrared region, preferably in the mid-infrared region. In an exemplary embodiment the apparatus 100 is configured to determine the presence of PMMA on bone. PMMA has an absorption peak at a wavenumber of approximately 1750 $cm^{-1}$ (wavelength approximately 5.71 micrometers). Bone does not absorb strongly at 1750 $cm^{-1}$. Neither PMMA nor bone have an absorption peak at a wavenumber of approximately 1650 $cm^{-1}$ (wavelength approximately 6.06 micrometers). The first and second wavelengths are therefore chosen to be approximately 5.71 and 6.01 micrometers, respectively. When the control module 116 generates a comparison value CV that exceeds a threshold value, the control signal 122 indicates that PMMA is present at the inspection site 106. When the control module 116 generates a comparison value CV that is less than a threshold value, the control signal 122 indicates that only bone is present at the inspection site 106.

In use, the apparatus 100 may be subject to unintentional movement that results from an operator's hand shaking or from other vibration. The apparatus 100 may be configured so the control module 116 makes the determination of which of two or more substances is present at the inspection site 106 at a rate sufficiently fast to obviate variances that may result from such movement of the apparatus 100. For example, the control module 116 may make the determination at a rate much greater than the rate of movement of the apparatus 100. In an exemplary embodiment, the wheel 502 of the band-pass pulse generator 410 rotates at a rate greater than about 3,600 rotations per minute so that the intensity of reflected light of each wavelength may be determined greater than about sixty times per second. That is much faster than "operator shake." In an exemplary embodiment, the apparatus 100 determines the intensity of light reflected at each wavelength from the inspection site 106 at a rate greater than about one-hundred times per second. If the control module 116 determines which material is present more than once for each particular inspection site 106, it may store such determinations and then generate the output signal 122 based on an average or other statistical representation of the stored determinations.

The present invention is described as having a separate optical transmission medium 110, 118 for directing light of the first and second wavelengths $\lambda_1$, $\lambda_2$, respectively. In an exemplary embodiment, each of the optical transmission mediums 110, 118 includes components (e.g., optical fibers) for transmitting light of the first wavelength $\lambda_1$, that are separate from components (e.g., optical fibers) for transmitting light of the second wavelength $\lambda_2$.

Although the present invention is described as applied to the field of orthopedics and for the removal of PMMA from bone, the invention is generally applicable to discerning the presence of a substance on a base material.

Although the application is described above as directing light to the inspection site for determine the presence of a substance, the invention is not limited to radiation of a particular wavelength. The teachings of the present invention may be generally applied by directing radiation of two different wavelengths to an inspection site for distinguishing between two different materials.

The foregoing describes the invention in terms of embodiments foreseen by the inventors for which an enabling description was available, although insubstantial modifications of the invention, not presently foreseen may nonetheless represent equivalents thereto.

What is claimed is:

1. A method for determining the presence or absence on a base material of a second material comprising the steps of:
   a. directing at an inspection site on a surface of said base material radiation of two different wavelengths, radiation of one of the wavelengths being more strongly absorbed by one material relative to its absorption by the other material and radiation of the other wavelength not displaying the same difference in absorption;
   b. measuring the intensity of reflected radiation resulting from the radiation directed at the inspection site; and
   c. determining the presence or absence of the second material at the inspection site based on the intensity of the reflected radiation resulting from directed radiation of one of the wavelengths relative to the intensity of the reflected radiation resulting from directed radiation of the other wavelength.

2. The method according to claim 1 wherein step (c) comprises comparing the intensity of the reflected radiation resulting from directed radiation of one of the wavelengths to a first absorption reference value to generate a first difference value, comparing the intensity of the reflected radiation resulting from directed radiation of the other wavelength to a second absorption reference value to generate a second difference value, and comparing the first and second difference values to determine a comparison value, a comparison value in excess of a preselected number being indicative of the presence of one of the materials at the inspection site.

3. The method according to claim 1 wherein step (a) comprises activating a radiation source to generate the radiation of the two different wavelengths and alternately positioning a first band-pass filter that passes radiation of one of the wavelengths and a second band-pass filter that passes radiation of the other wavelength between the radiation source and the inspection site or alternatively between the inspection site and a detector of the reflected radiation.

4. The method according to claim 1 wherein step (a) comprises activating a first coherent radiation source to generate radiation of one of the wavelengths and activating a second coherent radiation source to generate radiation of the other wavelength.

5. The method according to claim 4 wherein the first and second coherent radiation sources are alternately activated to alternately direct radiation each of the two different wavelengths at the inspection site.

6. The method according to claim 1 wherein the radiation of one of the wavelengths has a wavenumber of approximately 1750 $cm^{-1}$.

7. A method for selectively removing one of two materials from an inspection site comprising the steps of determining whether the second material is present at the inspection site according to the method of claim 1 and selectively removing one of the materials from the inspection site responsive to the determination.

8. The method according to claim 1, further comprising moving said inspection site over a surface of said base material, and determining where on said surface said second material is present.

9. The method according to claim 8, further comprising selectively removing material from said surface where it is determined that said second material is present.

10. The method according to claim 8, wherein radiation of said one wavelength is more strongly absorbed by said second material than by said base material and radiation of said other wavelength is not substantially more strongly absorbed by said second material than by said base material, further comprising selectively removing material from said surface where said first wavelength is absorbed substantially more strongly than said second wavelength.

11. The method according to claim 10 of removing cement from bone, wherein the radiation of said one of the wavelengths has a wavenumber of approximately 1750 cm$^{-1}$.

12. A method for determining whether a substance is present on a base material at an inspection site comprising the steps of:
 a. directing light of a first wavelength at an inspection site on a surface of the base material;
 b. determining a first inspection site absorption value corresponding to absorption of the light of the first wavelength directed at the inspection site;
 c. calculating a first difference value by comparing the first inspection site absorption value to a first absorption reference value;
 d. directing light of a second wavelength at the inspection site;
 e. determining a second inspection site absorption value corresponding to absorption of the light of the second wavelength directed at the inspection site;
 f. calculating a second difference value by comparing the second inspection site absorption value to a second absorption reference value; and
 g. generating an output signal indicating whether the substance is present at the inspection site based on the difference between the first difference value and the second difference value;
wherein the substance absorbs one of said first and second wavelengths substantially more than the other of said first and second wavelengths, and the base material absorbs said first and second wavelengths more equally than the substance.

13. An apparatus for distinguishing between two different materials comprising:
 a. a radiation module for generating radiation of two different wavelengths and directing the radiation to an inspection site on a surface of one of the materials;
 b. a detector module for receiving radiation reflected from the inspection site and generating a corresponding reflection signal; and
 c. a control module for receiving the reflection signal, determining which of the two materials is exposed at the inspection site based on whether the intensity of reflected radiation of one of the wavelengths relative to the intensity of reflected radiation of the other wavelength is substantially different from or similar to the intensity of the directed radiation of said one wavelength relative to the intensity of the directed radiation of said other wavelength, and generating an output signal indicating which of the two materials is present exposed at the inspection site.

14. The apparatus according to claim 13 wherein the radiation module comprises a first coherent radiation source that generates radiation of one of the wavelengths and a second coherent radiation source that generates radiation of the other wavelength.

15. The apparatus according to claim 14 wherein the control module is coupled to the radiation module and controls the radiation module to alternately activate the first and second coherent radiation sources.

16. The apparatus according to claim 13 wherein the radiation module comprises a quantum cascade laser.

17. The apparatus according to claim 13 wherein the radiation module comprises a non-coherent radiation source, a first band-pass filter that passes radiation of one of the wavelengths, a second band-pass filter that passes radiation of the other wavelength, and a pulse generator for alternately passing the first and second band-pass filters between the non-coherent radiation source and the inspection site.

18. The apparatus according to claim 13 further comprising a first optical transmission medium for directing radiation from the radiation module to the inspection site and a second optical transmission medium for directing the reflected radiation to the detector module.

19. A device for selectively removing one of two different materials from an inspection site, the device comprising an apparatus according to claim 13 for determining which of the two materials is exposed at the inspection site and a removal apparatus for selectively removing said one of the materials from the inspection site responsive to the output signal.

20. An apparatus according to claim 13, wherein said radiation module and said detector module are arranged to be movable for moving said inspection site over a surface, said control module generating an output signal indicating where on said surface either of the two materials is exposed.

21. An apparatus according to claim 20 for endoscopic or arthroscopic cleaning of bone, further comprising removal apparatus for selectively removing one of said materials from the inspection site responsive to the output signal.

* * * * *